(12) United States Patent
Lin et al.

(10) Patent No.: US 9,809,805 B2
(45) Date of Patent: Nov. 7, 2017

(54) ZINC BINDING FUSION PROTEIN OF GLUTATHIONE S-TRANSFERASE AND METALLOTHIONEIN

(71) Applicant: Acro Biotech Co., Ltd., New Taipei (TW)

(72) Inventors: Chiao-Wei Lin, Taipei (TW); Tang-Long Shen, Taipei (TW); Ko-Chien Chen, Taipei (TW); Jer-Li Lin, Taipei (TW); Sheng-Hong Tsai, Taipei (TW)

(73) Assignee: ACRO BIOTECH CO., LTD., New Taipei (TW)

( * ) Notice: Subject to any disclaimer, the term of this patent is extended or adjusted under 35 U.S.C. 154(b) by 0 days.

(21) Appl. No.: 15/069,215

(22) Filed: Mar. 14, 2016

(65) Prior Publication Data

US 2016/0264947 A1    Sep. 15, 2016

Related U.S. Application Data

(60) Provisional application No. 62/132,738, filed on Mar. 13, 2015.

(51) Int. Cl.
*A61K 38/17* (2006.01)
*C12N 9/10* (2006.01)
*C07K 14/825* (2006.01)
*A61K 38/00* (2006.01)

(52) U.S. Cl.
CPC .......... *C12N 9/1088* (2013.01); *C07K 14/825* (2013.01); *C12Y 205/01018* (2013.01); *A61K 38/00* (2013.01); *C07K 2319/00* (2013.01)

(58) Field of Classification Search
CPC .............................. A61K 38/17; A61K 31/713
See application file for complete search history.

(56) References Cited

U.S. PATENT DOCUMENTS 9,327,012 B2 *    5/2016    Kokai .................. C07K 14/825

FOREIGN PATENT DOCUMENTS

WO    2012115185    *    8/2012

OTHER PUBLICATIONS

Jamakala et al., International Journal of Pharmacy and Pharmaceutical Sciences, vol. 6(9), Sep. 2014.*

* cited by examiner

*Primary Examiner* — Maryam Monshipouri
(74) *Attorney, Agent, or Firm* — Birch, Stewart, Kolasch & Birch, LLP

(57) ABSTRACT

The present invention relates to a new zinc binding fusion protein that is a fusion protein of glutathione S-transferase (GST) and metallothionein (MT), to which zinc bind, providing an efficacy in preventing or treating a ROS-related disease and heavy metal poisoning.

11 Claims, 6 Drawing Sheets

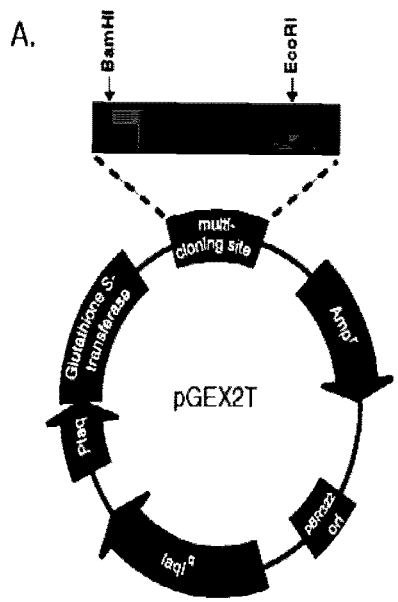

Figure 1A

B. (pGEX2T)  BamHI tatagcatggcctttgcagggctggcaagccacgtttggtggtggcgaccatcct
ccaaaatcggatctggttccgcgtggatccATGGACCCTGAGACCTGCC
CCTGCCCTTCTGGTGGCTCCTGCACCTGCGCGGACTCCTGCA
AGTGCGAGGGATGCAAATGCACCTCCTGCAAGAAGAGCTGC
TGCTCCTGCTGCCCTGCGGAGTGTGAGAAGTGTGCCAAGGA
CTGTGTGTGCAAAGGCGGAGAGGCAGCTGAGGCAGAAGCA
GAGAAGTGCAGCTGCTGCCAGTGgaaggcacccctc

Figure 1B

SEQUENCE LISTING

```
<160> NUMBER OF SEQ ID NOS: 32

<210> SEQ ID NO 1
<211> LENGTH: 68
<212> TYPE: PRT
<213> ORGANISM: Homo sapiens

<400> SEQUENCE: 1

Met Asp Pro Glu Thr Cys Pro Cys Pro Ser Gly Gly Ser Cys Thr Cys
1               5                   10                  15

Ala Asp Ser Cys Lys Cys Glu Gly Cys Lys Cys Thr Ser Cys Lys Lys
            20                  25                  30

Ser Cys Cys Ser Cys Cys Pro Ala Glu Cys Glu Lys Cys Ala Lys Asp
        35                  40                  45

Cys Val Cys Lys Gly Gly Glu Ala Ala Glu Ala Glu Ala Glu Lys Cys
    50                  55                  60

Ser Cys Cys Gln
65

<210> SEQ ID NO 2
<211> LENGTH: 67
<212> TYPE: PRT
<213> ORGANISM: Tursiops truncatus

<400> SEQUENCE: 2

Met Asp Pro Glu Thr Cys Pro Cys Pro Thr Gly Gly Ser Cys Thr Cys
```

```
                1               5                   10                  15
Ala Asp Ser Cys Lys Cys Glu Gly Cys Lys Cys Thr Ser Cys Lys Lys
            20                  25                  30

Ser Cys Cys Ser Cys Cys Pro Ala Glu Cys Glu Lys Cys Ala Lys Asp
        35                  40                  45

Cys Val Cys Lys Gly Gly Glu Gly Ala Glu Ala Glu Glu Lys Cys Ser
    50                  55                  60

Cys Cys Gln
65

<210> SEQ ID NO 3
<211> LENGTH: 68
<212> TYPE: PRT
<213> ORGANISM: Callithrix jacchus

<400> SEQUENCE: 3

Met Asp Pro Glu Pro Cys Pro Cys Pro Ser Gly Gly Ser Cys Thr Cys
1               5                   10                  15

Ala Asp Ser Cys Lys Cys Glu Gly Cys Lys Cys Thr Ser Cys Lys Lys
            20                  25                  30

Ser Cys Cys Ser Cys Cys Pro Ala Glu Cys Lys Lys Cys Ala Lys Asp
        35                  40                  45

Cys Val Cys Lys Gly Gly Glu Gly Thr Glu Ala Glu Ala Glu Lys Cys
    50                  55                  60

Ser Cys Cys Gln
65

<210> SEQ ID NO 4
<211> LENGTH: 68
<212> TYPE: PRT
<213> ORGANISM: Vicugna pacos

<400> SEQUENCE: 4

Met Asp Pro Glu Thr Cys Pro Cys Pro Thr Gly Gly Ser Cys Thr Cys
1               5                   10                  15

Ala Gly Ser Cys Lys Cys Glu Gly Cys Lys Cys Thr Ser Cys Lys Lys
            20                  25                  30

Ser Cys Cys Ser Cys Cys Pro Glu Glu Cys Glu Lys Cys Ala Lys Asp
        35                  40                  45

Cys Ala Cys Lys Gly Gly Glu Gly Ala Glu Ala Glu Glu Lys Cys
    50                  55                  60

Ser Cys Cys Gln
65

<210> SEQ ID NO 5
<211> LENGTH: 68
<212> TYPE: PRT
<213> ORGANISM: Canis lupus familiaris

<400> SEQUENCE: 5

Met Asp Pro Glu Thr Cys Pro Cys Pro Thr Gly Gly Ser Cys Thr Cys
1               5                   10                  15

Asp Gly Ser Cys Lys Cys Glu Gly Cys Lys Cys Thr Ser Cys Lys Lys
            20                  25                  30

Ser Cys Cys Ser Cys Cys Pro Ala Glu Cys Glu Lys Cys Ala Lys Asp
        35                  40                  45

Cys Val Cys Lys Gly Gly Glu Gly Thr Glu Ala Glu Ala Glu Lys Cys
    50                  55                  60
```

Ser Cys Cys Gln
65

<210> SEQ ID NO 6
<211> LENGTH: 66
<212> TYPE: PRT
<213> ORGANISM: Oryctolagus cuniculus

<400> SEQUENCE: 6

Met Asp Pro Glu Ser Cys Pro Cys Pro Thr Gly Gly Ser Cys Thr Cys
1               5                   10                  15

Glu Asp Ser Cys Lys Cys Gln Gly Cys Lys Cys Thr Ser Cys Lys Lys
            20                  25                  30

Ser Cys Cys Ser Cys Cys Pro Ala Glu Cys Glu Lys Cys Ala Lys Asp
        35                  40                  45

Cys Val Cys Lys Gly Gly Gly Ala Glu Ala Glu Lys Cys Ser Cys
    50                  55                  60

Cys Gln
65

<210> SEQ ID NO 7
<211> LENGTH: 66
<212> TYPE: PRT
<213> ORGANISM: Cavia porcellus

<400> SEQUENCE: 7

Met Asp Pro Glu Thr Cys Pro Cys Pro Thr Gly Gly Ser Cys Thr Cys
1               5                   10                  15

Ala Asn Ser Cys Lys Cys Glu Asp Cys Lys Cys Thr Asp Cys Lys Lys
            20                  25                  30

Ser Glu Cys Ser Cys Cys Pro Ala Glu Cys Glu Lys Cys Ala Lys Asp
        35                  40                  45

Cys Val Cys Lys Gly Gly Glu Gly Val Lys Ala Glu Glu Lys Cys
    50                  55                  60

Ser Cys
65

<210> SEQ ID NO 8
<211> LENGTH: 68
<212> TYPE: PRT
<213> ORGANISM: Sus scrofa

<400> SEQUENCE: 8

Met Asp Pro Glu Thr Cys Pro Cys Pro Thr Gly Gly Ser Cys Ser Cys
1               5                   10                  15

Ala Gly Ser Cys Thr Cys Lys Ala Cys Arg Cys Thr Ser Cys Lys Lys
            20                  25                  30

Ser Cys Cys Ser Cys Cys Pro Ala Glu Cys Glu Lys Cys Ala Lys Asp
        35                  40                  45

Cys Val Cys Lys Gly Gly Glu Gly Ala Glu Ala Glu Glu Lys Cys
    50                  55                  60

Ser Cys Cys Gln
65

<210> SEQ ID NO 9
<211> LENGTH: 66
<212> TYPE: PRT
<213> ORGANISM: Ochotona princeps

```
<400> SEQUENCE: 9

Met Asp Pro Glu Thr Cys Pro Cys Pro Ser Gly Gly Ser Cys Thr Cys
1               5                   10                  15

Glu Asp Ser Cys Lys Cys Gln Gly Cys Lys Cys Thr Ser Cys Lys Lys
            20                  25                  30

Ser Cys Cys Ser Cys Cys Pro Ala Glu Cys Glu Lys Cys Ala Lys Asp
        35                  40                  45

Cys Val Cys Lys Gly Glu Gly Ala Glu Ala Glu Lys Cys Ser Cys
    50                  55                  60

Cys Gln
65

<210> SEQ ID NO 10
<211> LENGTH: 57
<212> TYPE: PRT
<213> ORGANISM: Pteropus vampyrus

<400> SEQUENCE: 10

Glu Thr Cys Thr Cys Pro Thr Gly Gly Ser Cys Thr Cys Ala Gly Ser
1               5                   10                  15

Cys Lys Cys Glu Gly Cys Lys Cys Thr Ser Cys Lys Lys Ser Cys Cys
            20                  25                  30

Ser Cys Cys Pro Ala Glu Cys Glu Lys Cys Thr Lys Asp Cys Ala Cys
        35                  40                  45

Lys Gly Gly Glu Gly Ala Glu Ala Glu
    50                  55

<210> SEQ ID NO 11
<211> LENGTH: 68
<212> TYPE: PRT
<213> ORGANISM: Felis catus

<400> SEQUENCE: 11

Met Asp Pro Glu Thr Cys Pro Cys Pro Thr Gly Gly Ser Cys Thr Cys
1               5                   10                  15

Asn Gly Ser Cys Lys Cys Glu Gly Cys Lys Cys Thr Ser Cys Lys Lys
            20                  25                  30

Ser Cys Cys Ser Cys Cys Pro Ala Glu Cys Glu Lys Cys Ala Lys Asp
        35                  40                  45

Cys Val Cys Lys Gly Glu Gly Gly Thr Glu Ala Glu Ala Glu Lys Cys
    50                  55                  60

Ser Cys Cys Gln
65

<210> SEQ ID NO 12
<211> LENGTH: 68
<212> TYPE: PRT
<213> ORGANISM: Pan troglodytes

<400> SEQUENCE: 12

Met Asp Pro Glu Thr Cys Pro Cys Pro Ser Gly Gly Ser Cys Thr Cys
1               5                   10                  15

Ala Asp Ser Cys Lys Cys Glu Gly Cys Lys Cys Thr Ser Cys Lys Lys
            20                  25                  30

Ser Cys Cys Ser Cys Cys Pro Ala Glu Cys Glu Lys Cys Ala Lys Asp
        35                  40                  45

Cys Val Cys Lys Gly Gly Glu Ala Ala Glu Ala Glu Ala Glu Lys Cys
    50                  55                  60
```

Ser Cys Cys Gln
65

<210> SEQ ID NO 13
<211> LENGTH: 68
<212> TYPE: PRT
<213> ORGANISM: Equus caballus

<400> SEQUENCE: 13

Met Asp Pro Glu Thr Cys Pro Cys Pro Thr Gly Gly Ser Cys Thr Cys
1               5                   10                  15

Ser Gly Ser Cys Lys Cys Glu Gly Cys Lys Cys Thr Ser Cys Lys Lys
            20                  25                  30

Ser Cys Cys Ser Cys Cys Pro Ala Glu Cys Glu Lys Cys Ala Lys Asp
        35                  40                  45

Cys Val Cys Lys Gly Gly Glu Gly Ala Glu Ala Glu Ala Glu Lys Cys
    50                  55                  60

Ser Cys Cys Gln
65

<210> SEQ ID NO 14
<211> LENGTH: 70
<212> TYPE: PRT
<213> ORGANISM: Myotis lucifugus

<400> SEQUENCE: 14

Met Asp Pro Glu Thr Cys Pro Cys Pro Thr Gly Gly Ser Cys Thr Cys
1               5                   10                  15

Ala Gly Ala Asp Ser Cys Lys Cys Glu Gly Cys Lys Cys Thr Ser Cys
            20                  25                  30

Lys Lys Ser Cys Cys Ser Cys Cys Pro Pro Glu Cys Glu Lys Cys Thr
        35                  40                  45

Lys Asp Cys Val Cys Lys Gly Gly Gly Pro Gly Ala Glu Ala Gln
    50                  55                  60

Lys Cys Ser Cys Cys Asp
65              70

<210> SEQ ID NO 15
<211> LENGTH: 68
<212> TYPE: PRT
<213> ORGANISM: Loxodonta Africana

<400> SEQUENCE: 15

Met Asp Pro Glu Thr Cys Pro Cys Pro Thr Gly Gly Ser Cys Thr Cys
1               5                   10                  15

Ser Gly Ser Cys Lys Cys Glu Gly Cys Lys Cys Thr Ala Cys Lys Lys
            20                  25                  30

Ser Cys Cys Ser Cys Cys Pro Ala Glu Cys Gln Lys Cys Ala Lys Asp
        35                  40                  45

Cys Val Cys Lys Gly Asp Glu Gly Ala Gln Ala Glu Ala Glu Lys Cys
    50                  55                  60

Ser Cys Cys Gln
65

<210> SEQ ID NO 16
<211> LENGTH: 68
<212> TYPE: PRT
<213> ORGANISM: Ictidomys tridecemlineatus

```
<400> SEQUENCE: 16

Met Asp Pro Glu Thr Cys Pro Cys Pro Thr Gly Gly Ser Cys Thr Cys
1               5                   10                  15

Thr Asp Ser Cys Lys Cys Glu Gly Cys Lys Cys Thr Asn Cys Lys Lys
            20                  25                  30

Ser Cys Cys Ser Cys Cys Pro Ala Glu Cys Glu Lys Cys Ala Lys Asp
        35                  40                  45

Cys Val Cys Lys Gly Gly Glu Gly Ala Glu Ala Glu Ala Glu Lys Cys
    50                  55                  60

Ser Cys Cys Gln
65

<210> SEQ ID NO 17
<211> LENGTH: 68
<212> TYPE: PRT
<213> ORGANISM: Dasypus novemcinctus

<400> SEQUENCE: 17

Met Asp Pro Glu Thr Cys Pro Cys Pro Thr Gly Gly Ser Cys Thr Cys
1               5                   10                  15

Ala Gly Ser Cys Lys Cys Glu Gly Cys Lys Cys Thr Ser Cys Lys Lys
            20                  25                  30

Ser Cys Cys Ser Cys Cys Pro Ala Glu Cys Glu Lys Cys Ala Lys Asp
        35                  40                  45

Cys Val Cys Lys Gly Gly Glu Gly Ala Glu Ala Glu Ala Glu Lys Cys
    50                  55                  60

Ser Cys Cys Gln
65

<210> SEQ ID NO 18
<211> LENGTH: 68
<212> TYPE: PRT
<213> ORGANISM: Otolemur garnettii

<400> SEQUENCE: 18

Met Asp Pro Glu Thr Cys Pro Cys Pro Ser Gly Gly Ser Cys Thr Cys
1               5                   10                  15

Thr Asp Ser Cys Lys Cys Glu Gly Cys Lys Cys Thr Ser Cys Lys Lys
            20                  25                  30

Ser Cys Cys Ser Cys Cys Pro Ala Glu Cys Glu Lys Cys Ala Lys Asp
        35                  40                  45

Cys Val Cys Lys Gly Gly Glu Gly Ala Glu Ala Glu Ser Glu Lys Cys
    50                  55                  60

Asn Cys Cys Gln
65

<210> SEQ ID NO 19
<211> LENGTH: 68
<212> TYPE: PRT
<213> ORGANISM: Ailuropoda melanoleuca

<400> SEQUENCE: 19

Met Asp Pro Glu Thr Cys Pro Cys Pro Thr Gly Gly Ser Cys Thr Cys
1               5                   10                  15

Asp Gly Thr Cys Lys Cys Glu Gly Cys Lys Cys Thr Ser Cys Lys Lys
            20                  25                  30

Ser Cys Cys Ser Cys Cys Pro Ala Glu Cys Glu Lys Cys Thr Lys Asp
        35                  40                  45
```

Cys Val Cys Lys Gly Gly Glu Gly Thr Glu Ala Glu Ala Glu Lys Cys
            50                  55                  60

Ser Cys Cys Gln
65

<210> SEQ ID NO 20
<211> LENGTH: 68
<212> TYPE: PRT
<213> ORGANISM: Echinops telfairi

<400> SEQUENCE: 20

Met Asp Pro Glu Thr Cys His Cys Pro Thr Gly Gly Thr Cys Thr Cys
1               5                   10                  15

Ala Gly Ser Cys Lys Cys Glu Gly Cys Lys Cys Thr Ser Cys Lys Lys
            20                  25                  30

Ser Cys Cys Ser Cys Cys Pro Ala Glu Cys Glu Lys Cys Ala Lys Asp
        35                  40                  45

Cys Val Cys Lys Gly Glu Glu Gly Ala Lys Pro Glu Ala Glu Lys Cys
            50                  55                  60

Ser Cys Cys Gln
65

<210> SEQ ID NO 21
<211> LENGTH: 68
<212> TYPE: PRT
<213> ORGANISM: Tarsius syrichta

<400> SEQUENCE: 21

Met Asp Pro Glu Thr Cys Pro Cys Pro Ser Gly Gly Ser Cys Thr Cys
1               5                   10                  15

Ser Asp Ser Cys Lys Cys Glu Gly Cys Lys Cys Thr Ser Cys Lys Lys
            20                  25                  30

Ser Cys Cys Ser Cys Cys Pro Ala Glu Cys Glu Lys Cys Ala Lys Asp
        35                  40                  45

Cys Val Cys Lys Gly Gly Glu Gly Ala Lys Ala Glu Ala Glu Lys Cys
            50                  55                  60

Asn Cys Cys Gln
65

<210> SEQ ID NO 22
<211> LENGTH: 68
<212> TYPE: PRT
<213> ORGANISM: Ovis aries

<400> SEQUENCE: 22

Met Asp Pro Glu Ala Cys Pro Cys Pro Thr Gly Gly Ser Cys Thr Cys
1               5                   10                  15

Ser Asp Ser Cys Lys Cys Glu Gly Cys Thr Cys Ala Ser Ser Lys Lys
            20                  25                  30

Ser Glu Cys Gly Cys Cys Pro Ala Glu Cys Glu Lys Cys Ala Lys Asp
        35                  40                  45

Cys Val Cys Lys Gly Gly Glu Gly Ala Glu Ala Glu Glu Lys Lys Cys
            50                  55                  60

Gly Cys Cys Gln
65

<210> SEQ ID NO 23
<211> LENGTH: 68

<212> TYPE: PRT
<213> ORGANISM: Tupaia belangeri

<400> SEQUENCE: 23

Met Asp Pro Glu Ala Cys Pro Cys Pro Ser Gly Gly Ser Cys Thr Cys
1               5                   10                  15

Thr Asp Ser Cys Lys Cys Glu Gly Cys Lys Cys Thr Ser Cys Lys Lys
                20                  25                  30

Ser Cys Cys Ser Cys Cys Pro Ala Glu Cys Glu Lys Cys Ala Lys Asp
            35                  40                  45

Cys Val Cys Lys Gly Gly Glu Gly Thr Glu Ala Glu Ala Glu Lys Cys
        50                  55                  60

Ser Cys Ser Gln
65

<210> SEQ ID NO 24
<211> LENGTH: 68
<212> TYPE: PRT
<213> ORGANISM: Bos Taurus

<400> SEQUENCE: 24

Met Asp Pro Glu Thr Cys Pro Cys Pro Thr Gly Gly Ser Cys Thr Cys
1               5                   10                  15

Ser Asp Pro Cys Lys Cys Glu Gly Cys Thr Cys Ala Ser Ser Lys Lys
                20                  25                  30

Ser Cys Cys Ser Cys Cys Pro Ala Glu Cys Glu Lys Cys Ala Lys Asp
            35                  40                  45

Cys Val Cys Lys Gly Gly Glu Gly Ala Glu Ala Glu Glu Lys Lys Cys
        50                  55                  60

Ser Cys Cys Gln
65

<210> SEQ ID NO 25
<211> LENGTH: 68
<212> TYPE: PRT
<213> ORGANISM: Papio Anubis

<400> SEQUENCE: 25

Met Asp Pro Glu Thr Cys Pro Cys Pro Ser Gly Gly Ser Cys Thr Cys
1               5                   10                  15

Ala Asp Ser Cys Lys Cys Glu Gly Cys Lys Cys Thr Ser Cys Lys Lys
                20                  25                  30

Ser Cys Cys Ser Cys Cys Pro Ala Glu Cys Glu Lys Cys Ala Lys Asp
            35                  40                  45

Cys Val Cys Lys Gly Gly Glu Gly Ala Glu Ala Glu Ala Glu Lys Cys
        50                  55                  60

Ser Cys Cys Glu
65

<210> SEQ ID NO 26
<211> LENGTH: 68
<212> TYPE: PRT
<213> ORGANISM: Pongo abelii

<400> SEQUENCE: 26

Met Asp Pro Glu Thr Cys Pro Cys Pro Ser Gly Gly Ser Cys Thr Cys
1               5                   10                  15

Ala Asp Ser Cys Lys Cys Glu Gly Cys Lys Cys Thr Ser Cys Lys Lys
                20                  25                  30

```
Ser Cys Cys Ser Cys Cys Pro Ala Glu Cys Glu Lys Cys Ala Lys Asp
        35                  40                  45

Cys Val Cys Lys Gly Gly Gly Ala Glu Ala Glu Ala Glu Lys Cys
    50                  55                  60

Ser Cys Cys Gln
65

<210> SEQ ID NO 27
<211> LENGTH: 68
<212> TYPE: PRT
<213> ORGANISM: Erinaceus europaeus

<400> SEQUENCE: 27

Met Asp Pro Glu Thr Cys Pro Cys Pro Ser Gly Gly Ser Cys Thr Cys
1               5                   10                  15

Thr Asp Ser Cys Lys Cys Glu Gly Cys Lys Cys Thr Ser Cys Lys Lys
                20                  25                  30

Ser Cys Cys Ser Cys Cys Pro Ala Glu Cys Glu Lys Cys Ala Lys Asp
        35                  40                  45

Cys Arg Cys Lys Asp Gly Glu Gly Ala Lys Thr Glu Ala Glu Lys Cys
    50                  55                  60

Ser Cys Cys Gln
65

<210> SEQ ID NO 28
<211> LENGTH: 68
<212> TYPE: PRT
<213> ORGANISM: Gorilla gorilla gorilla

<400> SEQUENCE: 28

Met Asp Pro Glu Thr Cys Pro Cys Pro Ser Gly Gly Ser Cys Thr Cys
1               5                   10                  15

Ala Asp Ser Cys Lys Cys Glu Gly Cys Lys Cys Thr Ser Cys Lys Lys
                20                  25                  30

Ser Cys Cys Ser Cys Cys Pro Ala Glu Cys Glu Lys Cys Ala Lys Asp
        35                  40                  45

Cys Val Cys Lys Gly Gly Glu Ala Ala Glu Ala Glu Ala Glu Lys Cys
    50                  55                  60

Ser Cys Cys Gln
65

<210> SEQ ID NO 29
<211> LENGTH: 68
<212> TYPE: PRT
<213> ORGANISM: Macaca mulatta

<400> SEQUENCE: 29

Met Asp Pro Glu Thr Cys Pro Cys Pro Ser Gly Gly Ser Cys Thr Cys
1               5                   10                  15

Ala Asp Ser Cys Lys Cys Glu Gly Cys Lys Cys Thr Ser Cys Lys Lys
                20                  25                  30

Ser Cys Cys Ser Cys Cys Pro Ala Glu Cys Glu Lys Cys Ala Lys Asp
        35                  40                  45

Cys Val Cys Lys Gly Gly Glu Gly Ala Glu Ala Glu Ala Glu Lys Cys
    50                  55                  60

Ser Cys Cys Glu
65
```

```
<210> SEQ ID NO 30
<211> LENGTH: 68
<212> TYPE: PRT
<213> ORGANISM: Chlorocebus sabaeus

<400> SEQUENCE: 30

Met Asp Pro Glu Thr Cys Pro Cys Pro Ser Gly Gly Ser Cys Thr Cys
1               5                  10                  15

Ala Asp Ser Cys Lys Cys Glu Gly Cys Lys Cys Thr Ser Cys Lys Lys
            20                  25                  30

Ser Cys Cys Ser Cys Cys Pro Ala Glu Cys Glu Lys Cys Ala Lys Asp
        35                  40                  45

Cys Val Cys Lys Gly Gly Glu Gly Ala Glu Ala Glu Ala Glu Lys Cys
    50                  55                  60

Ser Cys Cys Glu
65

<210> SEQ ID NO 31
<211> LENGTH: 68
<212> TYPE: PRT
<213> ORGANISM: Mus musculus

<400> SEQUENCE: 31

Met Asp Pro Glu Thr Cys Pro Cys Pro Thr Gly Gly Ser Cys Thr Cys
1               5                  10                  15

Ser Asp Lys Cys Lys Cys Lys Gly Cys Lys Cys Thr Asn Cys Lys Lys
            20                  25                  30

Ser Cys Cys Ser Cys Cys Pro Ala Gly Cys Glu Lys Cys Ala Lys Asp
        35                  40                  45

Cys Val Cys Lys Gly Glu Glu Gly Ala Lys Ala Glu Ala Glu Lys Cys
    50                  55                  60

Ser Cys Cys Gln
65

<210> SEQ ID NO 32
<211> LENGTH: 66
<212> TYPE: PRT
<213> ORGANISM: Rattus norvegicus

<400> SEQUENCE: 32

Met Asp Pro Glu Thr Cys Pro Cys Pro Thr Gly Gly Ser Cys Thr Cys
1               5                  10                  15

Ser Asp Lys Cys Lys Cys Lys Gly Cys Lys Cys Thr Asn Cys Lys Lys
            20                  25                  30

Ser Cys Cys Ser Cys Cys Pro Ala Gly Cys Glu Lys Cys Ala Lys Asp
        35                  40                  45

Cys Val Cys Lys Gly Glu Glu Gly Ala Lys Ala Glu Lys Cys Ser Cys
    50                  55                  60

Cys Gln
65
```

ZINC BINDING FUSION PROTEIN OF GLUTATHIONE S-TRANSFERASE AND METALLOTHIONEIN

CROSS REFERENCE TO RELATED APPLICATIONS

This non-provisional application claims the benefit under 35 U.S.C. §119(e) to U.S. Provisional Application No. 62/132,738, filed on Mar. 13, 2015, all of which are hereby expressly incorporated by reference into the present application.

FIELD OF THE INVENTION

The present invention relates to a new zinc binding fusion protein, particularly a fusion protein comprising glutathione S-transferase and metallothionein, to which zinc binds.

BACKGROUND OF THE INVENTION

Metallothioneins (MTs) are ubiquitous low molecular weight proteins and polypeptides of extremely high metal and cysteine content which give rise to metal-thiolate clusters. The MT gene family consists of four subfamilies designated MT1 through MT4. Increasing evidence shows that mammalian MT1/MT2 isoforms are involved in zinc homeostasis and protection against heavy metal toxicity and oxidative stress. MT3 is expressed mainly in neurons but also in glia; MT4 is mostly present in differentiating stratified squamous epithelial cells.

Vallee and Margoshe disclosed MT from purification of a Cd-binding protein from horse (equine) renal cortex. (Margoshes & Vallee, "A cadmium protein from equine kidney cortex". Journal of the American Chemical Society 79 (17): 4813-4814, 1957) There are four main isoforms expressed in humans (family 1, see chart below): MT1 (subtypes A, B, E, F, G, H, L, M, X), MT2, MT3, MT4. The different isoforms of MTs are found in different tissues in mammalians. For example, MT1 and MT2 are generally found in all organs, MT4 is mainly expressed in stratified tissues, but MT3 predominately exists in brain. MT3, which is also named growth inhibitory factor (GIF).

MTs play an important role in transcription factor regulation, thus malignant transformation of cells and ultimately cancer would be caused by the problems with MT function or expression. (Krizkova et al., "Metallothionein—a promising tool for cancer diagnostics". Bratisl Lek Listy 110 (2): 93-7, 2009.) It was found that the expression of MTs increased in some cancers of the breast, colon, kidney, liver, skin (melanoma), lung, nasopharynx, ovary, prostate, mouth, salivary gland, testes, thyroid and urinary bladder; and MT expression decreased in hepatocellular carcinoma and liver adenocarcinoma. (Cherian, "Metallothioneins in human tumors and potential roles in carcinogenesis". Mutation Research/Fundamental and Molecular Mechanisms of Mutagenesis 533: 201-209, 2003.)

Heavy metal toxicity has been proposed as a hypothetical etiology of autism, and dysfunction of MT synthesis. However, MT dysfunction has not specifically been linked to autistic spectrum disorders. It was reported in a study investigating children exposed to the vaccine preservative thiomersal in 2006 that levels of MT and antibodies to MT in autistic children did not differ significantly from non-autistic children. (Singh & Hanson, "Assessment of metallothionein and antibodies to metallothionein in normal and autistic children having exposure to vaccine-derived thimerosal". Pediatr Allergy Immunol 17 (4): 291-6, 2006.)

Accordingly, it is desirable to develop new fusion proteins related to metallothioneins that satisfy a need in the art by providing new diagnostic or therapeutic agents.

BRIEF SUMMARY OF THE INVENTION

This invention is based on the unexpected finding of a new zinc binding fusion protein that is a fusion protein of glutathione S-transferase (GST) and metallothionein (MT), to which Zinc binds, providing unexpectedly superior therapeutic efficacies in treating reactive oxygen species (ROS)-related diseases and heavy metal poisoning caused by acute or chronic exposure to heavy metal.

Accordingly, in one aspect, the present invention provides a zinc binding fusion protein of GST and MT (GST-MT-Zn). In one example of the invention, the GST-MT-Zn is GST-MT3-Zn.

In another aspect, the present invention provides a method for preventing or treating a ROS-related disease in a subject comprising administering to said subject an effective amount of the zinc binding fusion protein GST-MT3-Zn.

In one yet aspect, the present invention provides a method for preventing or treating heavy metal poisoning in a subject caused by acute or chronic exposure to heavy metal in a subject comprising administering to said subject an effective amount of the zinc binding fusion protein GST-MT3-Zn.

In a further aspect, the present invention provides a pharmaceutical composition comprising the zinc binding fusion protein (GST-MT3-Zn) according to the invention, and a pharmaceutically acceptable carrier.

It is believed that a person of ordinary knowledge in the art where the present invention belongs can utilize the present invention to its broadest scope based on the descriptions herein with no need of further illustration. Therefore, the following descriptions should be understood as of demonstrative purpose instead of limitative in any way to the scope of the present invention.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1A shows the constructed expression vector pGEX2T, containing human MT3. FIG. 1B shows the sequence of MT3 cDNA on the pGEX2T expression vector.

DETAILED DESCRIPTION OF THE INVENTION

Figure 2:
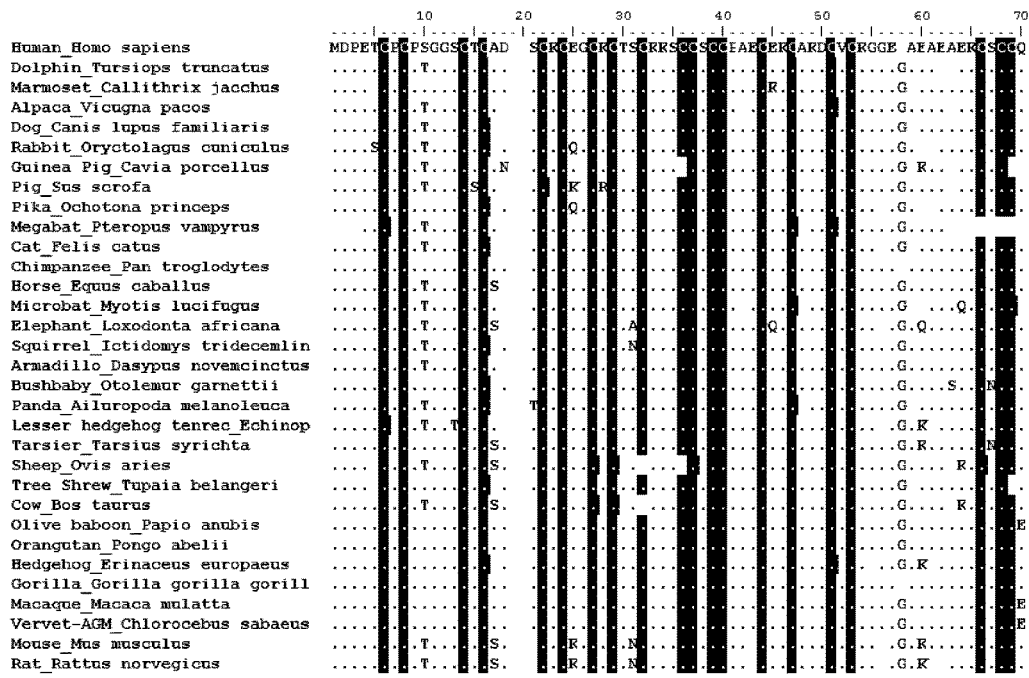
FIG. 2 provides the alignment of the MT3 amino acid sequences, showing the appearance of the conserved key cysteine residues, which implicates the same functional relevance, among varied animal species.

Unless otherwise defined, all technical and scientific terms used herein have the same meaning as commonly understood by one of ordinary skill in the art to which this invention pertains. In the case of conflict, the present document, including definitions will control.

As used herein, the singular forms "a", "an", and "the" include plural referents unless the context clearly dictates otherwise. Thus, for example, reference to "a sample" includes a plurality of such samples and equivalents thereof known to those skilled in the art.

As used herein, the term "a fusion protein of glutathione S-transferase and metallothionein," "a fusion protein of GST and MT," or "GST-MT" refers to a fusion protein of glutathione S-transferase (GST) and metallothionein (MT) or a functional variant thereof. The fusion protein may further comprise one or more chemical modification. The fusion protein may be fused in the way that GST is fused to N-terminal of the MT, or the MT is fused to N-terminal of the GST.

As used herein, the term "GST-MT-Zn" refers to a fusion protein of GST and MT, to which zinc binds.

As used herein, the term "metallothionein" refers to a family of genes encoding cysteine-rich, low molecular weight proteins which bind heavy metals (such as Zn and Cu) through the thiol group of their cysteine (Cys) residues. Metallothioneins are present in a variety of organisms including bacteria, fungi and all eukaryotic plant and animal species. There are four main isoforms of metallothionein: MT1, MT2, MT3, and MT4.

As used herein, the term "substitution" of an amino acid in a peptide refers to the replacement in a peptide of one amino acid with another amino acid. The amino acid is replaced with another amino acid having similar structural and/or chemical properties, e.g., conservative amino acid replacements. The "conservative" amino acid substitutions may be made on the basis of similarity in polarity, charge, solubility, hydrophobicity, hydrophilicity, and/or the amphipathic nature of the residues involved.

As used herein, the term "modification" of a peptide refers to any manipulation of the peptide backbone (e.g. amino acid sequence) or the post-translational modifications (e.g. glycosylation) of a polypeptide.

The term "vector" as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The term "host cell" refers to a cell into which exogenous nucleic acid has been introduced. A host cell is any type of cellular system that can be used to generate the fusion proteins of the present invention.

As used herein, the term "pharmaceutically acceptable carrier" means a chemical composition with which an appropriate compound or derivative can be combined and which, following the combination, can be used to administer the appropriate compound to a subject.

As used herein, the term "reactive oxygen species-related diseases" or "ROS-related diseases" refers to diseases caused by the adverse biological effects in the presence of abnormal levels of reactive oxygen species (ROS). Abnormal levels of reactive oxygen species (ROS) may participate in the pathogenesis in a large number of diseases. Examples of ROS-related diseases include obesity, insulin resistance, diabetes mellitus, alcoholic liver disease, inflammatory disease, sepsis, and heavy metal poisoning.

According to the present invention, a zinc binding fusion protein of a glutathione S-transferase (GST) and a metallothionein is provided, wherein the GST may be fused to N-terminal of the MT; or the MT may be fused to N-terminal of the GST. The MT may be MT1, MT2, MT3, or MT4 from any animal species.

In one example of the invention, the zinc binding fusion protein is a zinc binding fusion protein of GST and MT3 (abbreviated a "GST-MT3-Zn"). The MT3 may be isolated from any animal species, including but not limited to human (*Homo sapiens*), dolphin (*Tursiops truncates*), marmoset (*Callithrix jacchus*), alpaca (*Vicugna pacos*), dog (*Canis lupus familiaris*), rabbit (*Oryctolagus cuniculus*), guinea pig (*Cavia porcellus*), pig (*Sus scrofa*), pika (*Ochotona princeps*), megabat (*Pteropus vampyrus*), cat (*Felis catus*), chimpanzee (*Pan troglodytes*), horse (*Equus caballus*), microbat (*Myotis lucifugus*), elephant (*Loxodonta Africana*), squirrel (*ktidomys tridecemlineatus*), armadillo (*Dasypus novemcinctus*), bushbaby (*Otolemur garnettii*), panda (*Ailuropoda melanoleuca*), lesser hedgehog tenrec (*Echinops telfairi*), tarsier (*Tarsius syrichta*), sheep (*Ovis aries*), tree Shrew (*Tupaia belangeri*), cow (*Bos Taurus*), olive baboon (*Papio Anubis*), orangutan (*Pongo abelii*), hedgehog (*Erinaceus europaeus*), gorilla (*Gorilla gorilla gorilla*), macaque (*Macaca mulatta*), vervet-AGM (*Chlorocebus sabaeus*), mouse (*Mus musculus*), Rat (*Rattus norvegicus*), as shown in FIG. 2.

In the examples of the invention, MT3 refers to any one of the amino acid sequences set forth in SEQ ID Nos:1-32. In one particular example, MT3 is human MT3, which has the amino acid sequence of SEQ ID No:1.

According to the present invention, the fusion protein may be produced by recombinant DNA technologies. For example, the fusion protein may be expressed in a suitable host cell which is transformed with a vector comprising the nucleic acid molecule encoding the fusion protein. Accordingly, the invention also provides the nucleic acid molecule encoding the fusion protein of the invention, the vector comprising the nucleic acid molecule, and the host cell transformed with the vector for preparing the fusion protein.

Furthermore, the fusion protein of GST and MT3 may be exposed to the zinc ions, such as the solution of a zinc containing base, such as zinc chloride or to allow zinc binding to the fusion protein through the thiol group of their cysteine (Cys) residues.

Figure 4:
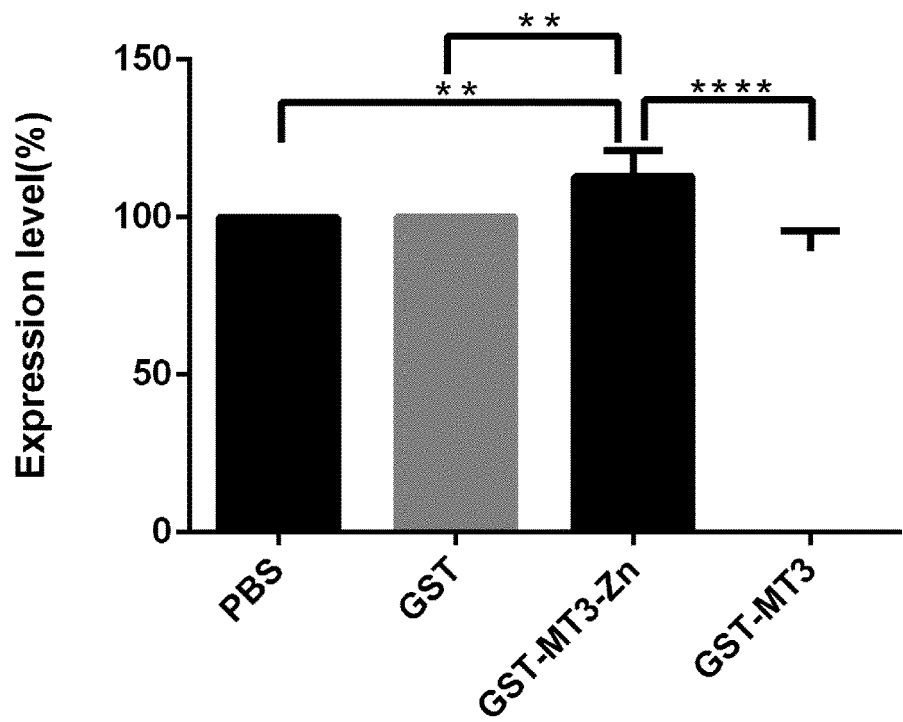
FIG. 4 shows the analyzation by PMOD 3.6 (PMOD Technologies, Zurich, Switzerland) of microPET brain scan of mice treated with PBS, GST, GST-MT3-Zn and GST-MT3, respectively. The mice were divided into 4 groups (n=3 for each group), and treated with PBS, GST, GST-MT3-Zn and GST-MT3 respectively at the concentration of 0.5 μg/200 μl, respectively via i.p., before receiving [$^{18}$F] FDG. The mice were then subjected to brain scans for 40 minutes using micro PET.

The fusion protein or zinc binding fusion protein of the invention may include any one with one or more chemical modifications without change of function. For example, the fusion protein may contain one or more substitution of amino acid It has been proved that the zinc binding fusion protein of GST and MT3 (GST-MT3-Zn) promoted brain activity, and unexpectedly GST-MT3-Zn had significant better efficacy than GST-MT3, as illustrated in FIG. 4.

Accordingly, the present invention provides a method for enhancing brain activity in a subject, comprising administering to said subject an effective amount of the GST-MT3-Zn. Alternatively, the prevention invention provides a use a use of the GST-MT3-Zn for manufacture of a medicament for enhancing brain activity.

Figure 5:
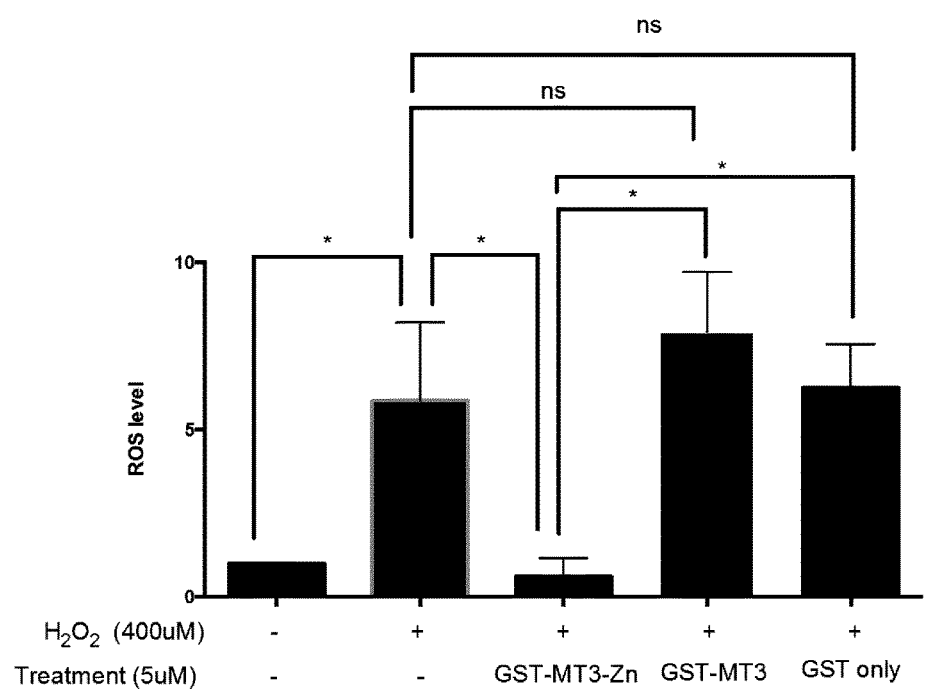
FIG. 5 shows the ROS levels of SK-N-SH neuronal cells treated with GST-MT3-Zn, GST-MT3 and GST for 30 minutes and challenged with $H_2O_2$ at 400 μM for 4 hours, respectively. Cells treated with GST-MT3-Zn seemingly acted as an anti-ROS scavenger compared to GST or GST-MT3 treatment. The measurements were performed in triplicate and the statistical analyses were derived at least 3 experiments. *$p<0.05$.

It has also been proved that the GST-MT3-Zn provides an improved anti-oxidant efficacy and metabolic activity, specifically in removing ROS, and unexpectedly GST-MT3-Zn had significant better efficacy than GST-MT3, as illustrated in FIG. 5.

Accordingly, the present invention provides a method for preventing or treating a ROS-related disease in a subject, comprising administering to said subject an effective amount of the GST-MT3-Zn. Alternatively, the prevention invention provides a use of the GST-MT3-Zn for manufacture of a medicament for preventing or treating a ROS-related disease.

In one embodiment of the invention, the ROS-related disease refers to a disease caused by the adverse biological effects in the presence of abnormal levels of reactive oxygen species (ROS). In the invention, the ROS-related disease is one selected from the group consisting of obesity, insulin resistance, diabetes mellitus, alcoholic liver disease, inflammatory disease, sepsis, and heavy metal poisoning.

Figure 6:
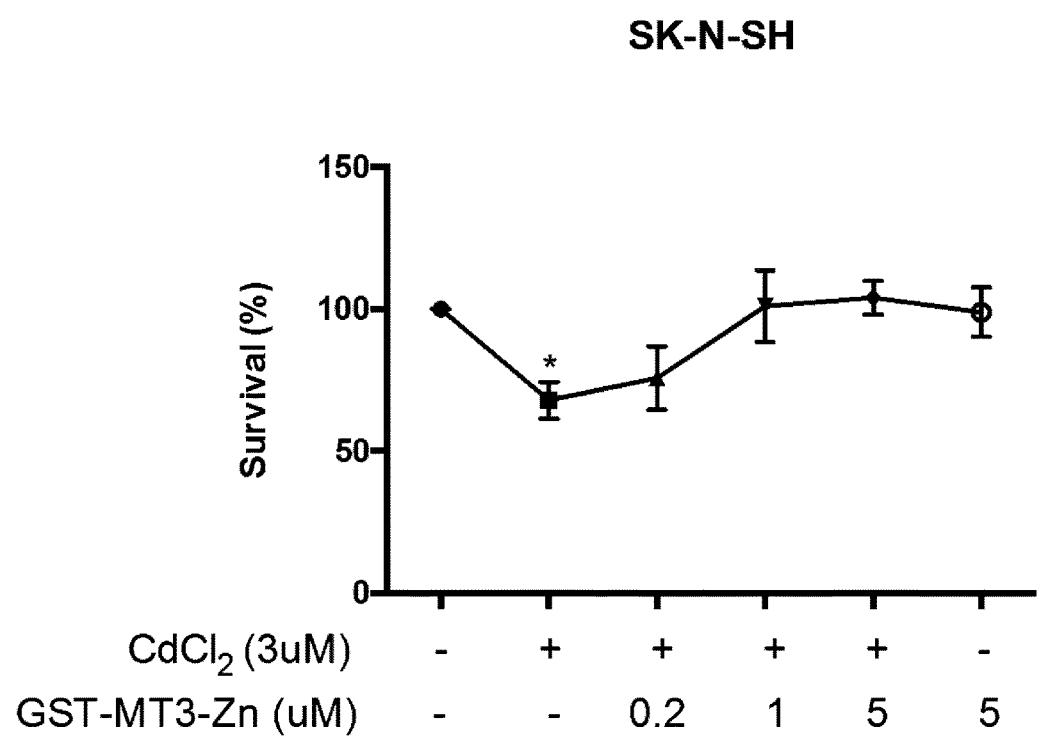
FIG. 6 shows the MIT assay result for SK-N-SH neuronal cells susceptible for Cd at 3 uM for 96 hours, and treated with 0.2 μM, 1 μM and 5 μM GST-MT3-Zn, respectively. Cells treated with GST-MT3-Zn at indicated concentrations exhibited a prominent rescue from the Cd-induced neuronal cell damage. The measurements were performed in triplicate and the statistical analyses were derived at least 3 experiments. *$p<0.05$.

It has further been proved that the GST-MT3-Zn provides a rescue effect on the viability of cells affected by exposure to heavy metal, for example, as illustrated in FIG. 6.

Accordingly, the present invention provides a method for preventing or treating heavy metal poisoning in a subject, comprising administering to said subject an effective amount of the GST-MT3-Zn. Alternatively, the prevention invention provides a use of the GST-MT3-Zn for manufacture of a medicament for preventing or treating heavy metal poisoning.

In one embodiment, the heavy metal which caused heavy metal poisoning is cadmium (Cd), lead (Pb), arsenic (As), mercury (Hg) chromium (Cr), copper (Cu), manganese (Mn), or nickel (Ni). In one specific embodiment, the heavy metal is cadmium (Cd).

For use in therapy, therapeutically effective amount of the protein, or functional variant thereof and any active ingredient may be formulated as a pharmaceutical composition for administration.

Accordingly, the present invention provides a pharmaceutical composition comprising the zinc binding fusion protein of glutathione S-transferase and a metallothionein 3 (GST-MT3-Zn), and a pharmaceutically acceptable carrier. The pharmaceutical composition may be formulated with any appropriate pharmaceutically acceptable carrier using conventional technologies.

Some examples below are provided to be construed as merely illustrative, and not limitative of the remainder of the disclosure in any way whatsoever. Without further elaboration, it is believed that one skilled in the art can, based on the description herein, utilize the present invention to its fullest extent.

EXAMPLE

1. DNA Cloning

Total RNAs were extracted from human embryonic kidney epithelial cells (HEK293 cells) by Qiagen mini RNA purification kit according to manufacturer's instructions. Then, approximate 100 ng of total RNAs were used for one-step RT-PCR in a 20-ul reaction mixture with corresponding primer set to MT3 as listed in Table 1. After reverse-transcription at 55° C. for 30 min, the PCR condition was performed at 94° C. for 5 min, followed by 35 cycles of 94° C. for 30 sec, 55° C. for 30 sec, and 72° C. for 30 sec. The reaction was completed and hold at 4° C. after 10 min at 72° C. These reactions were carried out in, a Veriti 96-well thermo cycler (Applied Biosystems, Calif., USA). The resulting PCR products were analyzed by electrophoresis on 1.5% agarose gel and eluted by QIAEX II Gel Extraction Kit. The obtained DNA fragments were then digested with BamHI and EcoRI following gel elution prior to ligation with a bacterial expression pGEX2T vector (containing an IPTG inducible promoter and an amino-terminal GST tag ahead of its multiple cloning sites) cut with BamHI and EcoRI as well. DNA ligation was proceeded at 16° C. for overnight. After transformation into BL21 competent cells, pGEX2T-MT3 construct was selected using the ampicillin resistant cassette and confirmed by DNA sequencing. The pET28a-MT3 was generated by obtaining the MT3 open reading frame from the pGEX2T-MT3 cut with NheI and XhoI and ligated with the pET28a vector on the corresponding sites. The pET28a-MT3 expression construct in BL21 cells produces a 6×his tag at the amino-terminus of MT3 named as His-MT3.

2. Protein Expression

The BL21 bacteria harboring the individual pGEX2T-MT3 expression construct aforementioned were cultured in 5 ml of LB broth containing 100 μg/ml ampicillin at 37° C. shaking with 250 rpm. Upon the $OD_{600nm}$ at 1.0, then 0.5 mM IPTG (isopyopyl-β-D-thiogalactopyranoside) plus 0.3 mM $ZnCl_2$ were added into the culture broth for induction of the recombinant protein expression for another 8 hours. The total cell lysates were spun down at 3000 g and re-suspended in 5 ml PBS following sonication by an 15-sec pause interval/per minute for 10 min at power level 4 using the Misonix Sonicator 3000. The supernatant was collected after spun at 13000 rpm at 4° C. for 10 min and then resuspended in 1 ml PBS prior to being subjected for GST-MT3 fusion protein purification by GST-agarose beads. The 20 mM reduced glutathione in 50 mM Tris-HCl pH 9.5 was used for the recombinant protein elution and followed size-exclusive chromatography (S-200) to obtain the pure GST-MT3 recombinant protein. The purified GST-MT3 recombinant proteins were then subjected for SDS-PAGE analyses in combination with coomassie blue staining to examine the expression of these pGEX2T-MT constructs in an IPTG inducible manner.

For massive production in fermentation, at first, a start-up 50 ml LB broth with ampicillin inoculated a single colony of BL21 bearing a pGEX2T-MT3 expression vector was cultured at 37° C. with 250 rpm for 16 hours. Then, the overnight culture broth was transferred into 500 ml of fresh LB medium containing ampicillin for further growth up to 10 at $OD_{600nm}$ before feed into the 5-liter fermentor with 4.5 liter fresh LB broth. The fermentation was carried out at 37°

C., 200 rpm, 15% $O_2$ and pH 7.0 for 24 hours in the presence of 1 mM IPTG while the $OD_{600nm}$ is 20. The bacteria were harvested by centrifugation at 13000 rpm for 10 min and then re-suspended in 100 ml PBS completely. Then the suspension was subjected for sonication (power level 4) at a 15 sec pause interval per min for 30 min on ice. The supernatant was kept after centrifugation at 13000 rpm, 30 min, for GST-affinity column purification. Before elution, 5 liters of PBS containing 1% Triton X114 were used to wash out potential endotoxin contamination.

To generate the MT3 alone recombinant protein, the purified GST-MT3 protein was cleaved by thrombin (Sigma) according to manufacturer's instructions. Briefly, 1 mg GST-MT3 protein bound on agarose beads was gently swirling to mix with 50-units thrombin protease (MW 37 kDa, ~4500 units/mg) in 1 ml PBS buffer for 16 hr at 22° C. Then, the reaction solution was spun for 4 min at 3000 rpm to pellet the beads. The supernatant was then carefully collected and stored in −80° C. Usually, the digested solution was checked by SDS-PAGE-SDS or subjected to separation and collection by FPLC chromatography.

Furthermore, the GST-MT3 protein was exposed to the solution of zinc ions, such as the solution of zinc chloride to allow zinc binding to the fusion protein through the thiol group of their cysteine (Cys) residues.

3. Western Blot Analyses

Firstly, the recombinant proteins were separated by electrophoresis on 15% SDS-PAGE. Then, the gel was transferred onto a nitrocellulose membrane. The membrane was subjected to blocking with 5% non-fat skim milk in TBST (137 mM NaCl, 2.7 mM KCl, 19 mM Tris base, 0.005% Tween-20, pH 7.4) for 1 hour before blotting with anti-GST (1:1000 dilution, Pierce) or anti-MT (1:1000 dilution, Sigma) polyclonal antibody in 5% BSA containing TBST for overnight at 4° C. on a shaker. Prior to adding HRP-conjugated secondary antibodies, the membrane was washed 5 min with TBST for three times. After 1 hour incubation and 3-times wash with TB ST, the result can be visualized on X-ray film in ECL detection system according to manufacturer's instructions.

4. Protein Mass Spectrophotometry

Mass spectrometry analyses of the recombinant GST-MT3 protein were performed at the Mithra Biotechnology Inc., Taipei, Taiwan, using 10 μg of FPLC purified proteins. The samples were reduced with 10 mM DTT at 37° C. for 1 hour and alkylated with 50 mM IAM in dark at RT for 30 min.

Then trypsin in 25 mM ammonium bicarbonate was added to perform digestion at 37° C. for 18 hours. Samples were analyzed with ESI-Q-TOF mass spectrometer (Bruker micrOTOF-Q II) coupled with Ultimate 3000 RSLC system (Dionex). The LC separation was performed using the C18 column (Acclaim PepMap RSLC, 75 μm×150 mm, 2 μm, 100 Å) with linear gradient from 1% to 30% of Mobile phase B (Mobile phase A: 5% ACN/0.1% FA, Mobile phase B: 95% ACN/0.1% FA) for 40 min, 80% of Mobile phase B for 10 min in a total of 70 min separation time. Full MS scan was performed with range m/z 350-2000 and the ten most intense ions from MS scan were selected for MS/MS scans. Raw data was processed into peak list by Proteome Discoverer 1.4 for Mascot database search.

5. Zinc Ion Detection by AA and ICP-OES

The atomic absorption spectroscopy (AA) was used for calculation of the zion binding to the fusion protein. The concentration of zinc ion was calculated in comparison with a standard curve. Alternatively, the quantitative measurement enabled conducted by the Inductively Coupled Plasma Optical Emission Spectrometry (ICP-OES, PerkinElmer® Optima™ 8000) technique. The GST-MT3-Zn protein was dissolved in 0.5 M nitric acid solution and then subjected to gel filtration in the S-200 FPLC. The concentration for zinc ion effectively detected is ranged from 0.1 to 50 ppm.

6. Evaluation of Brain Activity Using MicroPET Scans

Animals

Twelve 6-weeks male C57BL/6 mice were divided into four groups of three mice (n=3) as follows: a mock group treated with PBS, a control group treated with GST, a tested group treated with GST-MT3-Zn (containing Zn) and a tested group treated with GST-MT3 (lacking Zn). The animals were kept under an environmentally controlled condition with 12 h light/dark cycle, 20-24 C and 40-70% relative humidity in cages with food and water ad libitum. This animal study was approved by the Institutional Animal Care and Use Committee of National Taiwan University.

Micro PET Scan and Analysis

The mice undergone starvation for 24 hours prior to being subjected for a single i.p. injection of treatments an hour before micro PET scans. The treatments of PBS, GST, GST-MT3-Zn and GST-MT3 were all at the same concentration of 0.5 μg/200 μl. Static micro PET scans were performed in National Taiwan University Hospital Molecular Imaging Center. For glucose metabolic analysis, mice first received 288.6±20 μCi [$^{18}$F]FDG via intraperitoneal injection and allowed a conscious uptake period time for 15 min. Then, the mice were immediately subjected to brain scans for 40 min. Anesthesia was induced by inhalation of isoflurane (5% for induction and 2% for maintenance during scanning) supplemented with oxygen. Acquired images were analyzed using PMOD 3.6 (PMOD technologies, Zurich, Switzerland).

7. Cell-Based ROS Scavenging Assay

Approximately $5\times10^3$ SK-N-SH cells were seeded in each well of a 96-well plate and exposed to the indicated GST, GST-MT3-Zn or GST-MT3 (without Zn) for 30 minutes after 16 hours of serum starvation. After $H_2O_2$ (400 μM) challenge for 4 hours, the cells were incubated with fluorescent probes (CM-H2DCFDA, Sigma, USA) for 30 minutes in a 37° C. incubator (light was excluded). Finally, the cells were trypsinized and subjected to ROS quantification via the detection of the DCF levels, which corresponded to the relative ROS amounts at 525 nm using a flow cytometer (BD FACSCanto™, USA). The measurements were performed in triplicate.

8. Cd Heavy Metal in Neuronal Cell MTT Assay

The MTT assay was used to measure the abilities of the tested heavy metals to induce human neuronal cell death. Approximately $5\times10^3$ cells were seeded onto each well of a 96-well plate containing 200 μl of culture medium (per well) 24 hours before treatment. After exposure to various concentrations of the indicated heavy metals for 96 hours, the cells were incubated with 20 μl of MTT (Thiazolyl Blue Tetrazolium Bromide, Sigma, USA) solution for 4 hours. Cell viability was measured by the absorption at 570 nm using a spectrophotometer (SpectraMax® 190 UV-Vis Microplate, Molecular Devices, USA). The measurements were performed in triplicate and the statistical analyses were derived at least 3 experiments. The percentages of viable cells were calculated as (sample $OD_{570}$ nm/Mock $OD_{570}$ nm)×100(%).

9. Amino Acid Sequence Alignment

The amino acid sequence of MT3 was obtained from the Ensemble Genome Browser.

10. Statistical Analyses

All data are expressed as the means±the SEMs based on at least three independent experiments. The statistical analyses were performed using one-way analyses of variance (ANOVA) followed by Tukey's tests, and significance was measured as indicated.

Results

1. Construction of Human Metallothioneins (MTs)

The pGEX2T expression vector was employed for generating human metallothionein protein expression constructs to produce GST-MT3 (see FIGS. 1A and 1B). The MT3 amino acid sequences were shown in Table 1, and the alignment of the MT3 amino acid sequences from various animal species is shown in FIG. 2. The pGEX2T vector contains an inducible lac promotor to drive massive protein expression up to 5-20% total protein amount of host $E.\ coli$ bacteria.

TABLE 1

The amino acid sequences of MT3 of various animal species

| Species | Sequence | SEQ ID No. |
|---|---|---|
| Human (*Homo sapiens*) | MDPETCPCPSGGSCTCADSCKCEGC KCTSCKKSCCSCCPAECEKCAKDCV CKGGEAAEA EAEKCSCCQ | SEQ ID No: 1 |
| Dolphin (*Tursiops truncatus*) | MDPETCPCPTGGSCTCADSCKCEGC KCTSCKKSCCSCCPAECEKCAKDCV CKGGEGAEAEEKCSCCQ | SEQ ID No: 2 |
| Marmoset (*Callithrix jacchus*) | MDPEPCPCPSGGSCTCADSCKCEGC KCTSCKKSCCSCCPAECKKCAKDCV CKGGEGTEAEAEKCSCCQ | SEQ ID No: 3 |
| Alpaca (*Vicugna pacos*) | MDPETCPCPTGGSCTCAGSCKCEGC KCTSCKKSCCSCCPEECEKCAKDCA CKGGEGAEAEEEKCSCCQ | SEQ ID No: 4 |
| Dog (*Canis lupus familiaris*) | MDPETCPCPTGGSCTCDGSCKCEGC KCTSCKKSCCSCCPAECEKCAKDCV CKGGEGTEAEAEKCSCCQ | SEQ ID No: 5 |
| Rabbit (*Oryctolagus cuniculus*) | MDPESCPCPTGGSCTCEDSCKCQGC KCTSCKKSCCSCCPAECEKCAKDCV CKGGEGAEAEKCSCCQ | SEQ ID No: 6 |
| Guinea Pig (*Cavia porcellus*) | MDPETCPCPTGGSCTCANSCKCEDC KCTDCKKSECSCCPAECEKCAKDCV CKGGEGVKAEEEKCSC | SEQ ID No: 7 |
| Pig (*Sus scrofa*) | MDPETCPCPTGGSCSCAGSCTCKAC RCTSCKKSCCSCCPAECEKCAKDCV CKGGEGAEAEEEKCSCCQ | SEQ ID No: 8 |
| Pika (*Ochotona princeps*) | MDPETCPCPSGGSCTCEDSCKCQGC KCTSCKKSCCSCCPAECEKCAKDCV CKGEEGAEAEKCSCCQ | SEQ ID No: 9 |
| Megabat (*Pteropus vampyrus*) | ETCTCPTGGSCTCAGSCKCEGCKCT SCKKSCCSCCPAECEKCTKDCACKG GEGAEAE | SEQ ID No: 10 |
| Cat (*Felis catus*) | MDPETCPCPTGGSCTCNGSCKCEGC KCTSCKKSCCSCCPAECEKCAKDCV CKGEEGTEAEAEKCSCCQ | SEQ ID No: 11 |
| Chimpanzee (*Pan troglodytes*) | MDPETCPCPSGGSCTCADSCKCEGC KCTSCKKSCCSCCPAECEKCAKDCV CKGGEAAEAEAEKCSCCQ | SEQ ID No: 12 |
| Horse (*Equus caballus*) | MDPETCPCPTGGSCTCSGSCKCEGC KCTSCKKSCCSCCPAECEKCAKDCV CKGGEGAEAEAEKCSCCQ | SEQ ID No: 13 |
| Microbat (*Myotis lucifugus*) | MDPETCPCPTGGSCTCAGADSCKCE GCKCTSCKKSCCSCCPPECEKCTKD CVCKGGEGPGAEAQKCSCCD | SEQ ID No: 14 |
| Elephant (*Loxodonta Africana*) | MDPETCPCPTGGSCTCSGSCKCEGC KCTACKKSCCSCCPAECQKCAKDC VCKGDEGAQAEAEKCSCCQ | SEQ ID No: 15 |
| Squirrel (*Ictidomys tridecemlineatus*) | MDPETCPCPTGGSCTCTDSCKCEGC KCTNCKKSCCSCCPAECEKCAKDCV CKGGEGAEAEAEKCSCCQ | SEQ ID No: 16 |

TABLE 1-continued

The amino acid sequences of MT3 of various animal species

| Species | Sequence | SEQ ID No. |
|---|---|---|
| Armadillo (Dasypus novemcinctus) | MDPETCPCPTGGSCTCAGSCKCEGC KCTSCKKSCCSCCPAECEKCAKDCV CKGGEGAEAEAEKCSCCQ | SEQ ID No: 17 |
| Bushbaby (Otolemur garnettii) | MDPETCPCPSGGSCTCTDSCKCEGC KCTSCKKSCCSCCPAECEKCAKDCV CKGGEGAEAESEKCNCCQ | SEQ ID No: 18 |
| Panda (Ailuropoda melanoleuca) | MDPETCPCPTGGSCTCDGTCKCEGC KCTSCKKSCCSCCPAECEKCTKDCV CKGGEGTEAEAEKCSCCQ | SEQ ID No: 19 |
| Lesser hedgehog tenrec (Echinops telfairi) | MDPETCHCPTGGTCTCAGSCKCEGC KCTSCKKSCCSCCPAECEKCAKDCV CKGEEGAKPEAEKCSCCQ | SEQ ID No: 20 |
| Tarsier (Tarsius syrichta) | MDPETCPCPSGGSCTCSDSCKCEGC KCTSCKKSCCSCCPAECEKCAKDCV CKGGEGAKAEAEKCNCCQ | SEQ ID No: 21 |
| Sheep (Ovis aries) | MDPEACPCPTGGSCTCSDSCKCEGC TCASSKKSECGCCPAECEKCAKDCV CKGGEGAEAEEKKCGCCQ | SEQ ID No: 22 |
| Tree Shrew (Tupaia belangeri) | MDPEACPCPSGGSCTCTDSCKCEGC KCTSCKKSCCSCCPAECEKCAKDCV CKGGEGAEAEAEKCSCCQ | SEQ ID No: 23 |
| Cow (Bos Taurus) | MDPETCPCPTGGSCTCSDPCKCEGC TCASSKKSCCSCCPAECEKCAKDCV CKGGEGAEAEEKKCSCCQ | SEQ ID No: 24 |
| Olive baboon (Papio Anubis) | MDPETCPCPSGGSCTCADSCKCEGC KCTSCKKSCCSCCPAECEKCAKDCV CKGGEGAEAEAEKCSCCE | SEQ ID No: 25 |
| Orangutan (Pongo abelii) | MDPETCPCPSGGSCTCADSCKCEGC KCTSCKKSCCSCCPAECEKCAKDCV CKGGEGAEAEAEKCSCCQ | SEQ ID No: 26 |
| Hedgehog (Erinaceus europaeus) | MDPETCPCPSGGSCTCTDSCKCEGC KCTSCKKSCCSCCPAECEKCAKDCR CKDGEGAKTEAEKCSCCQ | SEQ ID No: 27 |
| Gorilla (Gorilla gorilla gorilla) | MDPETCPCPSGGSCTCADSCKCEGC KCTSCKKSCCSCCPAECEKCAKDCV CKGGEAAEAEAEKCSCCQ | SEQ ID No: 28 |
| Macaque (Macaca mulatta) | MDPETCPCPSGGSCTCADSCKCEGC KCTSCKKSCCSCCPAECEKCAKDCV CKGGEGAEAEAEKCSCCE | SEQ ID No: 29 |
| Vervet-AGM (Chlorocebus sabaeus) | MDPETCPCPSGGSCTCADSCKCEGC KCTSCKKSCCSCCPAECEKCAKDCV CKGGEGAEAEAEKCSCCE | SEQ ID No: 30 |
| Mouse (Mus musculus) | MDPETCPCPTGGSCTCSDKCKCKGC KCTNCKKSCCSCCPAGCEKCAKDC VCKGEEGAKAEAEKCSCCQ | SEQ ID No: 31 |
| Rat (Rattus norvegicus) | MDPETCPCPTGGSCTCSDKCKCKGC KCTNCKKSCCSCCPAGCEKCAKDC VCKGEEGAKAEKCSCCQ | SEQ ID No: 32 |

2. Expression and Purification of GST-MT3 Recombinant Proteins

The expression and purification of the GST-MT3 recombinant proteins was revealed by 15% SDS-PAGE and visualized by coommassie blue staining. The GST-MT3 recombinant proteins was verified by Western blotting. Result of the purification for the GST-MT3 recombinant protein was shown in Table 2. The purity of the GST-MT3 was higher than either His-MT3 or MT3.

3. Identification of GST-MT3 Recombinant Protein

In addition to Western blotting as described above, the purified GST-MT3 recombinant protein was subjected for protein mass spectrophotometry analyses to warrant its identity.

TABLE 2

The purification characterization of GST-MT3

|  | Flask | Amino Acid Residues | Micromoles/liter | Purity (%) | Thrombin Cleavage | Chromatography | Elution | Fermentor |
|---|---|---|---|---|---|---|---|---|
| GST-MT3 | 85 mg/liter | 301 | 2.46 | 97 | X | GST column | 20 mM glutathione-reduced | 0.8 grams/4.5 liter |
| His-MT3 | 23 mg/liter | 74 | 2.7 | 74 | X | His-Taq column | Stepwise 150 mM imidazole | X |
| MT3 | 4.5 mg/liter | 68 | 0.58 | 94 | ¢ | Gel filtration | X | X |

It was found that approximate 85% coverage of the GST-MT3 was obtained in the MS/MS scan derived from an ESI-Q-TOF mass spectrometer to GST and human MT3 protein, indicating that the procedure used in the invention for expression and purification of the GST-MT3 recombinant protein was effective.

4. Zinc Ion Binding Capacity of GST-MT35. GST-MT3-Zn Promotes Brain Activity

Figure 3:
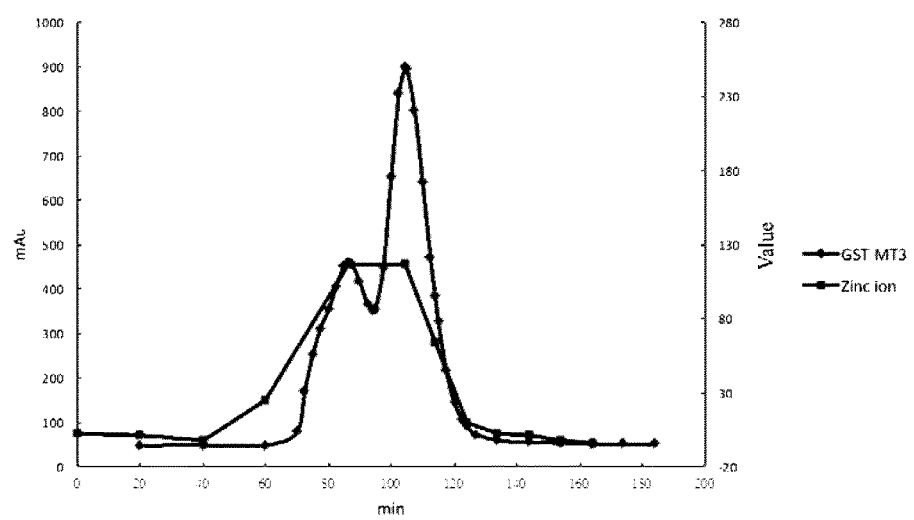
FIG. 3 shows the zinc binding capacity of GST-MT3.

Given the overlapping of GST-MT3 protein (by ICP) and zinc ion (by AA), it appears the co-existence of these two molecules (see FIG. 3). According to the molar ratio of these two molecules, each GST-MT3 protein estimates containing approximate 7 zinc ions.

Mice were divided into 4 groups (n=3 for each group) treated with PBS, GST, GST-MT3-Zn or GST-MT3 at the concentration of 0.5 μg/200 μl for each treatment via i.p. before receiving [$^{18}$F]FDG. Then, the mice were subjected to brain scans for 40 min using a micro PET. The images were analyzed using PMOD 3.6 (PMOD technologies, Zurich, Switzerland). As shown in FIG. 4, the results showed that the GST-MT3-Zn predominantly promoted brain activity compared to negative controls (PBS and GST) and GST-MT3 lacking Zn, as shown FIG. 4.

6. GST-MT3-Zn Exhibits a ROS Scavenger Activity

SK-N-SH neuronal cells were susceptible for $H_2O_2$ at 400 uM. As shown in FIG. 5, cells treated with GST-MT3-Zn seemingly acted as an anti-ROS scavenger compared to GST or GST-MT3 (lacking Zn) treatment. The measurements were performed in triplicate and the statistical analyses were derived at least 3 experiments. *p<0.05.

7. GST-MT3-Zn Detoxifies Cd-Induced Neuron Damage

SK-N-SH neuronal cells were susceptible for Cd at 3 uM. As shown in FIG. 6, cells treated with GST-MT3-Zn at indicated concentrations exhibited a prominent rescue from the Cd-induced neuronal cell damage. The measurements were performed in triplicate and the statistical analyses were derived at least 3 experiments. *p<0.05.

It is concluded that the zin-binding fusion protein GST-MT3-Zn according to the present invention enhances the brain activity, which is better than GST-MT3. In addition, it is indicated that GST-M3-Zn has an improved anti-antioxidant efficacy and a prominent rescue from the heavy metal-induced neuronal cell damage.

While this invention has been disclosed with reference to specific embodiments, it is apparent that other embodiments and variations of this invention may be devised by others skilled in the art without departing from the true spirit and scope of the invention.

We claim:

1. A protein GST-MT3-Zn, which is composed of glutathione S-transferase (GST), metallothionein3 (MT3) and zinc (Zn).

2. The protein GST-MT3-Zn of claim 1, wherein the MT3 is a human MT3.

3. The protein GST-MT3-Zn of claim 2, wherein the human MT3 has the amino acid sequence of SEQ ID No: 1.

4. A pharmaceutical composition comprising the protein GST-MT3-Zn of claim 1 and a pharmaceutically acceptable carrier.

5. A pharmaceutical composition of claim 4, wherein the MT3 is a human MT3.

6. A method for preventing or treating a ROS-related disease comprising administering to said subject an effective amount of the protein GST-MT3-Zn of claim 1.

7. The method of claim 6, wherein the ROS-related disease is heavy metal poisoning.

8. The method of claim 7, wherein the heavy metal is cadmium (Cd), lead (Pb), arsenic (As), mercury (Hg) chromium (Cr), copper (Cu), manganese (Mn) or nickel (Ni).

9. The method of claim 8, wherein the heavy metal is cadmium (Cd).

10. The method of claim 6, in which the protein GST-MT3-Zn enhances brain activity.

11. The method of claim 6, in which the protein GST-MT3-Zn enhances ROS scavenging activity in neuronal cells.

* * * * *